(12) United States Patent
Klein et al.

(10) Patent No.: US 8,907,045 B2
(45) Date of Patent: Dec. 9, 2014

(54) BIOCOMPATIBLE ADHESIVE POLYMERS

(75) Inventors: Josef Peter Klein, Vashon, WA (US); Floyd Brian Karp, Seattle, WA (US); Yansong Gu, Bellevue, WA (US); Roger A. Sahm, Snohomish, WA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/823,291

(22) PCT Filed: Apr. 3, 2012

(86) PCT No.: PCT/US2012/031998
§ 371 (c)(1),
(2), (4) Date: Mar. 14, 2013

(87) PCT Pub. No.: WO2013/151537
PCT Pub. Date: Oct. 10, 2013

(65) Prior Publication Data
US 2014/0041802 A1  Feb. 13, 2014

(51) Int. Cl.
| C08G 69/10 | (2006.01) |
| A61L 24/04 | (2006.01) |
| C08G 69/40 | (2006.01) |
| C09J 187/00 | (2006.01) |
| C09J 177/04 | (2006.01) |
| C09J 189/00 | (2006.01) |

(52) U.S. Cl.
CPC ............... *A61L 24/046* (2013.01); *C08G 69/40* (2013.01); *C09J 187/005* (2013.01); *C09J 177/04* (2013.01); *C09J 189/00* (2013.01); *C08G 69/10* (2013.01)
USPC ........... 528/328; 525/408; 525/420; 525/430; 525/434; 525/436

(58) Field of Classification Search
CPC ........ C08G 69/08; C08G 69/10; C08G 69/40; C08G 69/46; C08G 69/48; C08G 81/00; C08L 77/04; C08L 87/00
USPC ........... 525/408, 420, 430, 434, 436; 528/328
See application file for complete search history.

(56) References Cited

U.S. PATENT DOCUMENTS

| 6,506,577 B1 | 1/2003 | Deming et al. |
| 7,399,860 B2 | 7/2008 | Kumar et al. |
| 7,618,937 B2 | 11/2009 | Messersmith et al. |
| 2004/0208845 A1 | 10/2004 | Michal et al. |
| 2006/0002881 A1 | 1/2006 | Peng et al. |
| 2009/0163845 A1 | 6/2009 | Meyer-Ingold |
| 2009/0298999 A1 | 12/2009 | Shull et al. |
| 2010/0055067 A1 | 3/2010 | Park |
| 2010/0113828 A1 | 5/2010 | Dalsin et al. |
| 2010/0197868 A1 | 8/2010 | Lee |

FOREIGN PATENT DOCUMENTS

| EP | 2 272 897 | 1/2011 |
| JP | 05-117385 | 5/1993 |
| JP | 2010-138137 | 6/2010 |
| WO | WO-03/082303 | 10/2003 |
| WO | WO 2006/003731 | 1/2006 |
| WO | WO-2008/071957 | 6/2008 |
| WO | WO-2008/134731 | 11/2008 |
| WO | WO-2009/134984 | 11/2009 |
| WO | WO-2010/077671 | 7/2010 |

OTHER PUBLICATIONS

Roberts, M.J., et al.; Advanced Drug Delivery Reviews, 2002, p. 459-476.*
Bajaj, I., et al.; Bioresource Technology, 2011, p. 5551-5561.*
Anderson, T.H., et al., "The contribution of DOPA and substrate-peptide adhesion and internal cohesion of mussel-inspired synthetic peptide films," (2010), Adv Funct Mater 20, pp. 4196-4205.
Blomley, M.J., et al., "Microbubble contrast agents: a new era in ultrasound," May 2001, BMJ, vol. 322, pp. 1222-1225.
Burzio, L.A., Waite, JH., "Cross-linking in adhesive quinoproteins: Studies with model decapeptides," (2000), Biochemistry 39, pp. 11147-11153.
Chawla, K, et al., "A novel low-friction surface for biomedical applications: Modification of poly(dimethylsiloxane) (PDMS) with poly ethylene glycol(PEG)-DOPA-lysine," (2009), J Biomed Mater Res 90A, pp. 742-749.
Dou, H., et al., "Synthesis and purification of mono-PEGylated insulin," 2007, Chem. Biol. Drug Res. 69, pp. 132-138.
Huang, K, et al. "Synthesis and characterization of self-assembling block copolymers containing bioadhesive end groups," (2002), Biomacromol 3, pp. 397-406.
Huang, K., et al., "Synthesis and Characterization of Self-Assembling Block Copolymers Containing Adhesive Moieties," Polymer Preprints, 2001, 42(2), pp. 147-148.
International Search Report and Written Opinion received for PCT/US2012/031998 mailed Jun. 5, 2012.
Kinstler, O., et al., "Mono-N-terminal poly(ethylene glycol)-protein conjugates," 2002, Adv Drug Deliv Rev 54, pp. 477-485.
Lee, B.P., et al., "Rapid gel formation and adhesion in photocurable and biodegradable block copolymers with high DOPA content," (2006), Macromol 39, pp. 1740-1748.
Lee, B.P., et al., "Synthesis and gelation of DOPA-modified poly(ethylene glycol) hydrogels," (2002), Biomacromol 3, pp. 1038-1047.
Lee, H., et al., "A reversible wet/dry adhesive inspired by mussels and geckos," (2007), Nature 448, pp. 338-342.
Nederberg, F., et al., "Simple Approach to Stabilized Micelles Employing Miktoarm Terpolymers and Stereocomplexes with Application in Paclitaxel Delivery," 2009, Biomacromolecules 10, pp. 1460-1468.
Samyn, P, Ruhe, J, Biesalski, M., "Polymerizable biomimetic vesicles with controlled local presentation of adhesive functional DOPA groups," (2010), Langmuir 26 (11), pp. 8573-8581.

(Continued)

*Primary Examiner* — Robert Jones, Jr.
(74) *Attorney, Agent, or Firm* — Foley & Lardner LLP

(57) ABSTRACT

Block co-polymers including a hydrophilic block and a hydrophobic poly(amino acid) block which further includes dihydroxyphenyl moieties are provided, as well as methods of making and using the same. Such block copolymers may be used to prepare biocompatible adhesives which display good adhesives properties in aqueous environments, including in in vivo applications.

20 Claims, 1 Drawing Sheet

(56) References Cited

OTHER PUBLICATIONS

Xi, Z-Y, et al. "A facile method for surface modification of hydrophobic polymer membranes based on the adhesive behavior of poly(DOPA) and poly(dopamine)," (2009), J Membr Sci 327, pp. 244-253.

Yamamoto, H, Hayakawa, T., "Synthesis and conformational study of poly(L-beta-3,4-dihydroxyphenyl-alpha-alanine," (1977), Polymer 18, pp. 979-983.

Zhao, H., et al., "Probing the adhesive footprints of *Mytilus californianus* byssus," (2006), J Biol Chem 281, pp. 11090-11096.

Chang, E. et al., "Tissue engineering using autologous microcirculatory beds as vascularized bioscaffolds," The FASEB Journal, 2009, vol. 23, pp. 906-915.

Chin, K, et al., "Hydrogel-perfluorocarbon composite scaffold promotes oxygen transport to immobilized cells," 2008, Biotechnol Prog 24, pp. 358-366.

Du, W. et al., "Synthesis, Characterization, and Aqueous Self-Assembly of Amphiphilic Poly(ethylene oxide)-Functionalized Hyperbranched Fluoropolymers," Journal of Polymer Science: Part A: Polymer Chemistry, 2010, vol. 48, pp. 34870133496.

Fast, J.P., et al., "Fluoropolymer-based emulsions for the intravenous delivery of sevoflurane," 2008, Anesthesiology 109, pp. 651-656.

International Preliminary Report on Patentability in Intl. Pat. Appln. No. PCT/US2011/043138 mailed Jan. 16, 2014 (7 pages).

International Search Report for Intl. Pat. Appln. No. PCT/US2011/043138, mailed on Aug. 26, 2011 (4 pages).

Khattak, S.F., et al., "Enhancing oxygen tension and cellular function in alginate cell encapsulation devices through the use of perfluorocarbons," 2007, Biotech Bioengineering 96, pp. 156-166.

Kim, HW, et al., "Artificial oxygen carriers as red blood cell substitutes: a selected review and current status," Artificial Organs 28, (2004), pp. 813-828.

Krafft, M.P., "Fluorocarbons and fluorinated amphiphiles in drug delivery and biomedical research," Advanced Drug Delivery Reviews, 2001, vol. 47, pp. 209-228.

Non-Final Office Action in U.S. Appl. No. 13/443,576 dtd Jul. 2, 2013 (10 pages).

Notice of Allowance in U.S. Appl. No. 13/443,576 dtd Dec. 4, 2013 (15 pages).

Notice of Allowance in U.S. Appl. No. 13/443,576 dtd Jan. 16, 2014 (10 pages).

Pitarresi, G., et al., "Fluorinated derivatives of a polyaspartamide bearing polyethylene glycol chains as oxygen carriers," Journal of Fluorine Chemistry, vol. 129, No. 11, Nov. 2008, pp. 1096-1103.

Radisic, M., et al., "Biomimetic approach to cardiac tissue engineering: oxygen carriers and channeled scaffolds," 2006, Tissue Eng 12.

Restriction Requirement in U.S. Appl. No. 13/443,576 dtd Feb. 22, 2013 (11 pages).

Stevens, K.R., et al., "Physiological function and transplantation of scaffold-free and vascularized human cardiac muscle tissue," Proceedings of the National Academy of Sciences, 2009, vol. 106, No. 39, pp. 16568-16573.

Tsunoda, S., et al., "Molecular design of polyvinylpyrrolidone-conjugated interleukin-6 for enhancement of in vivo thrombopoietic activity in mice," Journal of Controlled Release, 2000, vol. 68, pp. 335-341.

Weinman, C.J., et al., "Antifouling block copolymer surfaces that resist settlement of barnacle larvae," 2007, PMSE Preprints 96, pp. 597-598.

\* cited by examiner

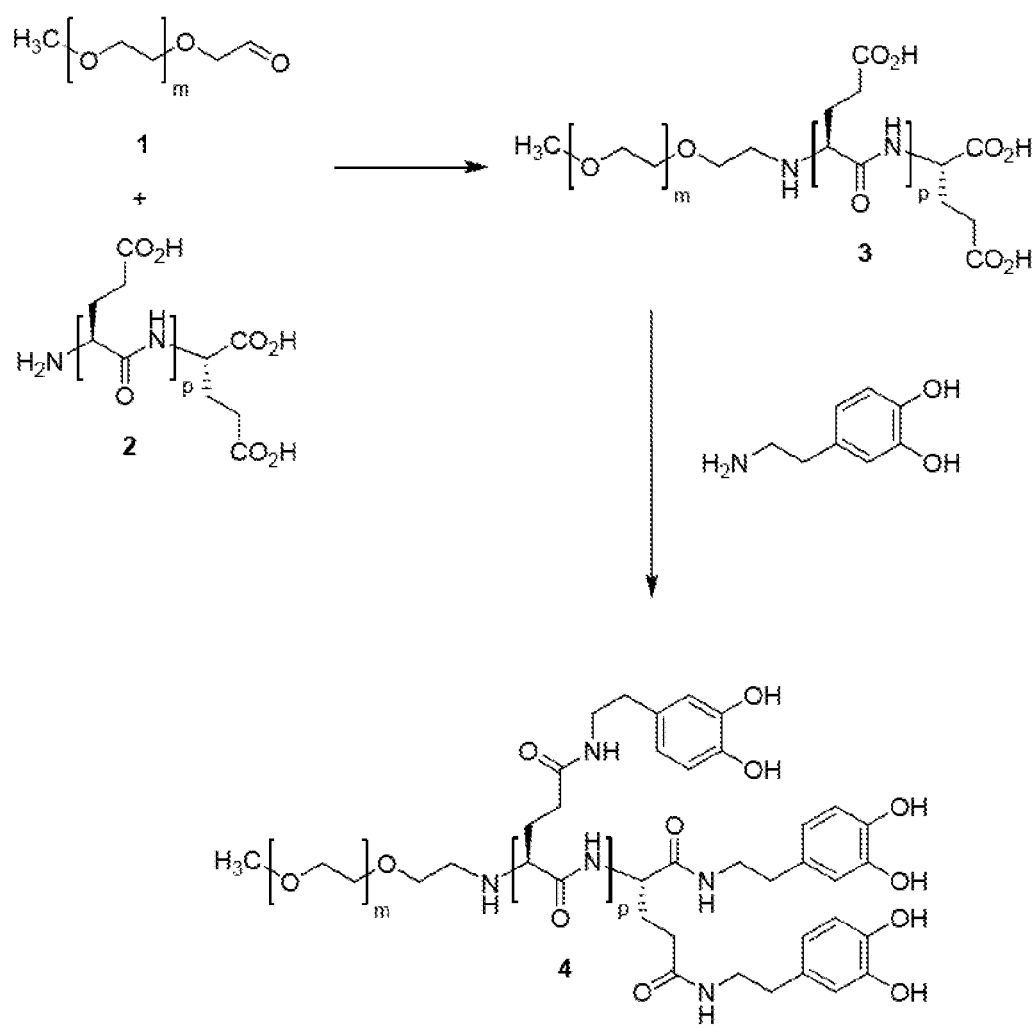

BIOCOMPATIBLE ADHESIVE POLYMERS

CROSS-REFERENCE TO RELATED APPLICATIONS

The present application is a U.S. national stage application of International Application No. PCT/US2012/031998, filed on Apr. 3, 2012, which is incorporated herein by reference in its entirety for any and all purposes.

FIELD

The present technology relates generally to biocompatible block co-polymers, adhesives prepared therefrom, and methods of making and using the same.

BACKGROUND

The following description is provided to assist the understanding of the reader. None of the information provided or references cited is admitted to be prior art to the present technology.

Water-compatible adhesive polymers have numerous applications in the biomedical field, including the joining of tissues to endogenous and exogenous materials. Biocompatible adhesive polymers find use in dental onlay adhesives and composites, bone cements, sealing of skin lacerations, wound dressing materials, attachment of engineered tissues, and attachment of medical device implants to tissues. Ideally, such adhesives should be non-immunogenic, biodegradable, and form innocuous degradation products. In situ activation of adhesive properties and rapid curing are also beneficial.

One strategy for improving the bioadhesive properties of polymers in aqueous environments is to introduce chemical groups which are known to possess such adhesive properties in nature. Mussel adhesive proteins are exceptional underwater adhesive materials which form tenacious bonds allowing for the anchoring of mussels to the substrates on which they reside. The amino acid 3-(3,4-dihydroxyphenyl)-L-alanine (DOPA) is a structural feature of mussel adhesive proteins and is thought to be responsible for both adhesion and cross-linking characteristics of mussel adhesive proteins. In particular, oxidation of DOPA to DOPA-quinone may lead to cross-linking of the mussel adhesive protein, while the dihydroxyphenyl form of DOPA is believed to be responsible for adhesion to substrates. However, simple introduction of DOPA or DOPA-like moieties into existing polymer architectures does not necessarily provide usable bioadhesives. For example, such groups may be prone to oxidation by air during storage, resulting in pre-mature (i.e., prior to use) cross-linking, and thus poor adhesion. Additionally, DOPA and DOPA-like moieties are prone to degradation by UV light.

SUMMARY

In accordance with one aspect, the present technology provides a block co-polymer of Formula I wherein, R is H or alkyl;

Y is —O—, —N(H)—, or —NC(O)alkylene-;

L is a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, or —N(R')C(O)N(R')alkylene-;

Q is a mono- or divalent radical of an amino acid side chain selected from a glutamic acid side chain, an aspartic acid side chain, a tyrosine side chain, a serine side chain, a threonine side chain, a lysine side chain, an ornithine side chain, a histidine side chain, an arginine side chain, a hydroxyarginine side chain, or an N-(3-hydroxypropyl)aspartamide side chain;

X is independently and at each occurrence a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, —N(R')C(O)N(R')alkylene-, —N(R')alkyleneN(R')—, —N(R')alkyleneC(O)N(R')—, —N(R')alkyleneN(R')C(=NR')N(R')—, —N(R')alkyleneN(R')C(=NR')N(R')O—, 3-oxylpyrrolidine-1,3-diyl, —C(O)alkyleneN(R')—, —C(O)alkyleneC(O)N(R')—, —C(O)alkyleneN(R')C(=NR')N(R')—, —C(O)alkyleneN(R')C(=NR')N(R')O—, or when taken together with Z is null;

Z is independently and at each occurrence selected from the group consisting of H, alkyl, and a group of Formula II or when taken together with X is null, wherein at least one occurrence of Z is the group of Formula II;

$Z^1$ is selected from the group consisting of H, alkyl, and a group of Formula II as defined above;

R' is independently and at each occurrence H or alkyl;

m is an integer from 0 to about 2000; and p is an integer from 1 to about 7000.

In some embodiments of the block co-polymer of Formula I, Y is —O—. In some embodiments, Y is —NC(O)(C$_1$-C$_8$ alkyl). In some embodiments, Y is —O—, —N(H)—, —NC(O)CH$_2$—, or —NC(O)CH$_2$CH$_2$—. In some embodiments, L is —O—CH$_2$CH$_2$— or —N(R')CH$_2$CH$_2$—. In some embodiments, R is H, methyl, or ethyl. In some embodiments, m is 0 or 1 to about 1000. In some embodiments, p is 1 to about 5000. In some embodiments, Q is a mono- or divalent radical of a glutamic acid side chain or an aspartic acid side chain. In some embodiments, —X—Z is null, —N(H)alkyl or —Oalkyl, or is a dihydroxyphenethylamine group. In some embodiments, —X—Z is a dihydroxyphenethylamine group which is dihydroxyphenethylamine (also known as dopamine), L-3,4-dihydroxyphenylalanine (L-DOPA), norepinephrine, or epinephrine. In some embodiments, about 10% to about 100% of the Z groups are the group of Formula II.

In some embodiments of the block co-polymer of Formula I, -Q-X—Z is one or more of —CH$_2$CO$_2$H, —CH$_2$CO$_2$CH$_2$(dihydroxyphenyl), —CH$_2$CO$_2$CH$_2$CH$_2$(dihydroxyphenyl), —CH$_2$C(O)NHCH$_2$(dihydroxyphenyl), —CH$_2$C(O)NHCH$_2$CH$_2$(dihydroxyphenyl), —CH$_2$CH$_2$CO$_2$H, —CH$_2$CH$_2$CO$_2$CH$_2$(dihydroxyphenyl), —CH$_2$CH$_2$CO$_2$CH$_2$CH$_2$(dihydroxyphenyl), —CH$_2$CH$_2$C(O)NHCH$_2$(dihydroxyphenyl), —CH$_2$CH$_2$C(O)NHCH$_2$CH$_2$(dihydroxyphenyl), —CH$_2$(1,4-C$_6$H$_4$)OH, —CH$_2$(1,4-C$_6$H$_4$)OCH$_2$(dihydroxyphenyl), —CH$_2$(1,4-C$_6$H$_4$)OCH$_2$CH$_2$(dihydroxyphenyl), —CH$_2$(1,4-C$_6$H$_4$)OC(O)(dihydroxyphenyl), —CH$_2$(1,4-C$_6$H$_4$)OC(O)CH$_2$(dihydroxyphenyl), —CH$_2$(1,4-C$_6$H$_4$)OC(O)CH$_2$CH$_2$(dihydroxyphenyl), —CH$_2$OH, —CH$_2$OCH$_2$(dihydroxyphenyl), —CH$_2$OCH$_2$CH$_2$(dihydroxyphenyl), —CH$_2$OC(O)(dihydroxyphenyl), —CH$_2$OC(O)CH$_2$(dihydroxyphenyl), —CH$_2$OC(O)CH$_2$CH$_2$(dihydroxyphenyl), —CH(CH$_3$)OH, —CH(CH$_3$)OCH$_2$(dihydroxyphenyl), —CH(CH$_3$)OCH$_2$CH$_2$(dihydroxyphenyl), —CH(CH$_3$)OC(O)(dihydroxyphenyl), —CH(CH$_3$)OC(O)CH$_2$(dihydroxyphenyl), —CH(CH$_3$)OC(O)CH$_2$CH$_2$(dihydroxyphenyl), —CH$_2$CH$_2$CH$_2$CH$_2$NH$_2$, —CH$_2$CH$_2$CH$_2$CH$_2$NHCH$_2$(dihydroxyphenyl), —CH$_2$CH$_2$CH$_2$CH$_2$NHCH$_2$CH$_2$(dihydroxyphenyl), —CH$_2$CH$_2$CH$_2$CH$_2$NHC(O)(dihydroxyphenyl), —CH$_2$CH$_2$CH$_2$CH$_2$NHC(O)CH$_2$(dihydroxyphenyl), —CH$_2$CH$_2$CH$_2$CH$_2$NHC(O)CH$_2$CH$_2$(dihydroxyphenyl), —CH$_2$CH$_2$CH$_2$NH$_2$, —CH$_2$CH$_2$CH$_2$NHCH$_2$(dihydroxyphenyl), —CH$_2$CH$_2$CH$_2$NHCH$_2$CH$_2$(dihydroxyphenyl), —CH$_2$CH$_2$CH$_2$NHC(O)(dihydroxyphenyl), —CH$_2$CH$_2$CH$_2$NHC(O)CH$_2$(dihydroxyphenyl), —CH$_2$CH$_2$CH$_2$NHC(O)CH$_2$CH$_2$(dihydroxyphenyl), —CH$_2$CH$_2$CH$_2$NHC(=NH)NH$_2$, —CH$_2$CH$_2$CH$_2$NHC(=NH)NHCH$_2$(dihydroxyphenyl), —CH$_2$CH$_2$CH$_2$NHC(=NH)NHCH$_2$CH$_2$(dihydroxyphenyl), —CH$_2$CH$_2$CH$_2$NHC(=NH)NHC(O)(dihydroxyphenyl), —CH$_2$CH$_2$CH$_2$NHC(=NH)NHC(O)CH$_2$(dihydroxyphenyl), —CH$_2$CH$_2$CH$_2$NHC(=NH)NHC(O)CH$_2$CH$_2$(dihydroxyphenyl), —CH$_2$CH$_2$CH$_2$NHC(=NH)NHOH, —CH$_2$CH$_2$CH$_2$NHC(=NH)NHOCH$_2$(dihydroxyphenyl), —CH$_2$CH$_2$CH$_2$NHC(=NH)NHOCH$_2$CH$_2$(dihydroxyphenyl), —CH$_2$CH$_2$CH$_2$NHC(=NH)NHOC(O)(dihydroxyphenyl), —CH$_2$CH$_2$CH$_2$NHC(=NH)NHOC(O)CH$_2$(dihydroxyphenyl), —CH$_2$CH$_2$CH$_2$NHC(=NH)NHOC(O)CH$_2$CH$_2$(dihydroxyphenyl),

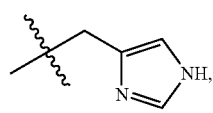

-continued

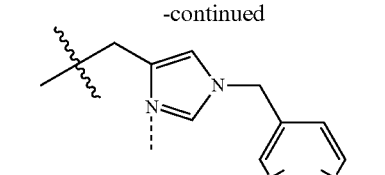

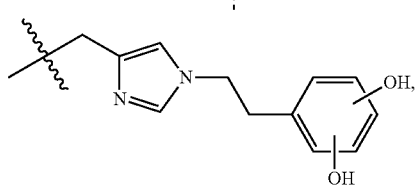

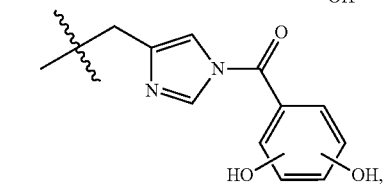

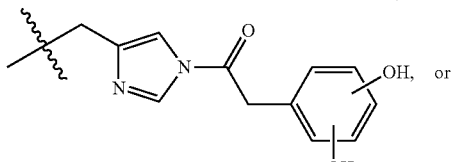

or

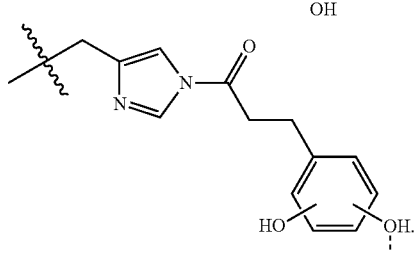

In accordance with another aspect, the present technology provides a block co-polymer including: a first block of poly(ethylene glycol) having a number average molecular weight of about 1,000 to about 10,000; and a second block of a poly(amino acid) homopolymer having a number average molecular weight of about 500 to about 100,000, wherein the poly(amino acid) homopolymer comprises dihydroxyphenyl groups linked to one or more of the amino acid side chain groups. In some embodiments, the amino acid side chain groups are selected from imidazoles, amines, hydroxyls, and carboxylates, guanidines, and hydroxyguanidines.

In accordance with another aspect, the present technology provides an adhesive including a block co-polymer of Formula I

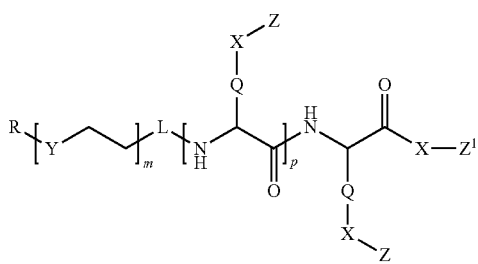

wherein,
R is H or alkyl;
Y is —O—, —N(H)—, or —NC(O)alkylene-;
L is a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, or —N(R')C(O)N(R')alkylene-;
Q is a mono- or divalent radical of an amino acid side chain selected from a glutamic acid side chain, an aspartic acid side chain, a tyrosine side chain, a serine side chain, a threonine side chain, a lysine side chain, an ornithine side chain, a histidine side chain, an arginine side chain, a hydroxyarginine side chain, or an N-(3-hydroxypropyl)aspartamide side chain;
X is independently and at each occurrence a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, —N(R')C(O)N(R')alkylene-, —N(R')alkyleneN(R')—, —N(R')alkyleneC(O)N(R')—, —N(R')alkyleneN(R')C(=NR')N(R')—, —N(R')alkyleneN(R')C(=NR')N(R')O—, 3-oxylpyrrolidine-1,3-diyl, —C(O)alkyleneN(R')—, —C(O)alkyleneC(O)N(R')—, —C(O)alkyleneN(R')C(=NR')N(R')—, —C(O)alkyleneN(R')C(=NR')N(R')O—, or when taken together with Z is null;
Z is independently and at each occurrence selected from the group consisting of H, alkyl, and a group of Formula II

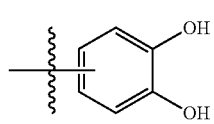

or when taken together with X is null, wherein at least one occurrence of Z is the group of Formula II;
Z¹ is selected from the group consisting of H, alkyl, and a group of Formula II as defined above;
R' is independently and at each occurrence H or alkyl;
m is an integer from 0 to about 2000; and
p is an integer from 1 to about 7000.

In some embodiments, the adhesive including the block co-polymer of Formula I further includes a peroxide. In some such embodiments, the peroxide is hydrogen peroxide.

In accordance with another aspect, the present technology provides a method of adhering together at least two substrates, the method including: applying an adhesive of Formula I to at least one substrate; and adhering together the substrates, wherein the adhesive has the Formula I

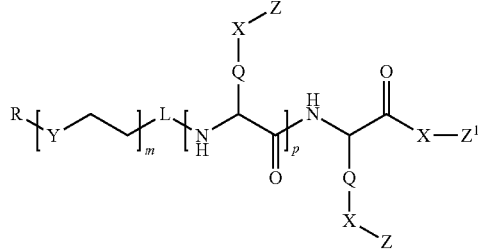

wherein,
R is H or alkyl;
Y is —O—, —N(H)—, or —NC(O)alkylene-;
L is a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, or —N(R')C(O)N(R')alkylene-;
Q is a mono- or divalent radical of an amino acid side chain selected from a glutamic acid side chain, an aspartic acid side chain, a tyrosine side chain, a serine side chain, a threonine side chain, a lysine side chain, an ornithine side chain, a histidine side chain, an arginine side chain, a hydroxyarginine side chain, or an N-(3-hydroxypropyl)aspartamide side chain;
X is independently and at each occurrence a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, —N(R')C(O)N(R')alkylene-, —N(R')alkyleneN(R')—, —N(R')alkyleneC(O)N(R')—, —N(R')alkyleneN(R')C(=NR')N(R')—, —N(R')alkyleneN(R')C(=NR')N(R')O—, 3-oxylpyrrolidine-1,3-diyl, —C(O)alkyleneN(R')—, —C(O)alkyleneC(O)N(R')—, —C(O)alkyleneN(R')C(=NR')N(R')—, —C(O)alkyleneN(R')C(=NR')N(R')O—, or when taken together with Z is null;
Z is independently and at each occurrence selected from the group consisting of H, alkyl, and a group of Formula II

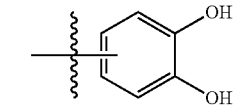

or when taken together with X is null, wherein at least one occurrence of Z is the group of Formula II;
Z¹ is selected from the group consisting of H, alkyl, and a group of Formula II as defined above;
R' is independently and at each occurrence H or alkyl;
m is an integer from 0 to about 2000; and
p is an integer from 1 to about 7000.

In some embodiments, at least one substrate is wetted. In some embodiments, at least one substrate is a tissue, such as bone tissue, tooth tissue, skin tissue, or organ tissue.

The foregoing summary is illustrative only and is not intended to be in any way limiting. In addition to the illustrative aspects, embodiments and features described above, further aspects, embodiments and features will become apparent by reference to the following drawings and the detailed description.

BRIEF DESCRIPTION OF THE DRAWINGS

FIG. 1 is a schematic illustration of the synthesis of compound 4 according to the Examples.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include substituted and unsubstituted straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups are unsubstituted alkyl groups and in others, substituted alkyl groups. Representative substituted alkyl groups may be mono-substituted or substituted more than once, such as, but not limited to, mono-, di- or tri-substituted with substituents such as those listed below.

Cycloalkyl groups are substituted or unsubstituted cyclic alkyl groups having from 3 to 10 carbon atoms. In some embodiments, the cycloalkyl group has 3 to 7 ring members, whereas in other embodiments the number of ring carbon atoms range from 3 to 5, 3 to 6, or 5, 6 or 7. Cycloalkyl groups further include monocyclic, bicyclic and tricyclic ring systems. Monocyclic groups include, e.g., cyclopropyl, cyclobutyl, cyclopentyl, cyclohexyl, and cycloheptyl groups. Bicyclic and tricyclic cycloalkyl groups include bridged or fused rings, such as, but not limited to, bicyclo[3.2.1]octane, decalinyl, and the like. Cycloalkyl groups include rings that are substituted with straight or branched chain alkyl groups as defined above. In some embodiments, the cycloalkyl groups are substituted cycloalkyl groups. Representative substituted cycloalkyl groups may be mono-substituted or substituted more than once, such as, but not limited to, mono-, di- or tri-substituted with substituents such as those listed below.

Alkenyl groups include substituted and unsubstituted straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2 to 4 carbon atoms. Examples include, but are not limited to vinyl, allyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, among others. Representative substituted alkenyl groups may be mono-substituted or substituted more than once, such as, but not limited to, mono-, di- or tri-substituted with substituents such as those listed above.

Aryl groups are substituted or unsubstituted cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above. Disbustituted aryl groups include, e.g., catechol, also known as 1,2-dihydroxyphenyl.

Aralkyl groups are alkyl groups as defined above in which a hydrogen or carbon bond of an alkyl group is replaced with a bond to an aryl group as defined above. Aralkyl groups may be unsubstituted or substituted on either the alkyl, the aryl or both groups. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above, and include, e.g., 1,2-dihydroxyphenylethyl.

The term "alkylene" alone or as part of another substituent refers to a divalent radical of an alkyl (including cycloalkyl) group. Each alkylene may be divalent at the same carbon or different carbons. Thus. e.g., the alkylene group based on ethyl is ethylene, and includes —CH($CH_3$)— as well as —$CH_2CH_2$—. For alkylene groups, no particular pattern of attachment or orientation of the group is implied.

"Substituted" refers to a chemical group as described herein that further includes one or more substituents (e.g., functional groups), such as acyl (C=O), halogen (F, Cl, Br, I), hydroxy (—OH), amine, ether (—O—), amide, ester, urethane, carboxy (COOH), nitro (—$NO_2$), cyano (—CN), thiol (—SH), sulfide, sulfonyl (—$SO_2$—), oxo (O=), and the like. These groups may be attached to any carbon or substituent of the alkyl or alkylene groups that is chemically permissible. The substituents may be pendent from, or integral to, the carbon chain itself. In some embodiments, the Additionally, cycloalkyl groups may be substituted by alkyl groups as defined herein.

The term "amine" (or "amino") as used herein refers to —NHR and —NRR' groups, wherein R, and R' are independently hydrogen, or a substituted or unsubstituted alkyl, alkenyl, cycloalkyl, aryl or aralkyl group as defined herein. Examples of amino groups include —$NH_2$, methylamino, dimethylamino, ethylamino, diethylamino, propylamino, isopropylamino, phenylamino, benzylamino, and the like.

The term "ester" as used herein refers to —COOR$^{30}$ groups. R$^{30}$ is a substituted or unsubstituted alkyl, cycloalkyl, alkenyl, aryl, or aralkyl group as defined herein.

The term "amide" (or "amido") includes C- and N-amide groups, i.e., —C(O)NR$^{31}$R$^{32}$, and —NR$^{31}$C(O)R$^{32}$ groups, respectively. $R^{31}$ and $R^{32}$ are independently hydrogen, or a substituted or unsubstituted alkyl, alkenyl, cycloalkyl, aryl, or aralkyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{33}$C(O)OR$^{34}$ and —OC(O)NR$^{33}$R$^{34}$ groups, respectively. $R^{33}$ and $R^{34}$ are independently a substituted or unsubstituted alkyl, alkenyl, cycloalkyl, aryl, or aralkyl group as defined herein. $R^{33}$ may also be H.

The present technology provides biocompatible block co-polymers including a hydrophilic block and a hydrophobic block, with one or more dihydroxyphenyl moieties attached to the hydrophobic block. The biocompatible polymers may be tuned as to possess a micellar structure, such that the dihydroxyphenyl moieties are disposed in the inner portion of the micelle. In this regard, the dihydroxyphenyl moieties are partially or fully protected from oxidation by air and degradation by UV light. Accordingly, adhesives prepared from the block co-polymers display improved shelf-stability (e.g., adhesive properties are maintained until use). In comparison to conventional adhesives, the present adhesives also display improved ability to bond to a variety of wet surfaces (both natural and synthetic), may be rapidly cured in situ, may be used over broad temperature ranges, and are fully compatible in water or other aqueous environments such as salt water and living systems. The block co-polymers and adhesives prepared therefrom will find application as biomedical adhesives (e.g., tissue adhesives, wound dressing materials, etc.), as well as in other water-contacting applications where benign adhesives may be desired. Finally, the present technology provides highly modular methods of preparing block co-polymers and adhesives, allowing for the expeditious and facile syntheses of custom-tailored materials with unique physical, chemical, and biological properties.

The biocompatible block co-polymers are comprised of materials such as poly(ethylene glycols) and protein-like polymers which degrade to innocuous and non-toxic byproducts. Such byproducts may include amino acids, peptides, and/or poly(ethylene glycol), each of which have well-established biocompatibilities. Indeed, poly(ethylene glycol) is a biocompatible polymer commonly employed in in vivo applications for drug delivery.

In accordance with another aspect, the present technology provides a block co-polymer of Formula I:

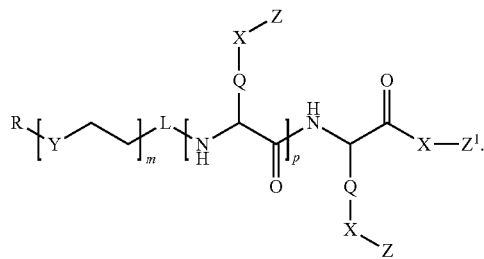

I

In the block co-polymer of Formula I, R is H or an alkyl group. The group Y is a heteroatom group such as —O—, —N(H)—, or —NC(O)alkylene-. Thus, as will be appreciated by those of skill in the art, the structural repeat unit m, which includes the group Y, corresponds to the hydrophilic block of the block co-polymer. For example, the hydrophilic block of the block co-copolymer may be a poly(ethylene glycol) or a poly(ethyleneimine) block. As will be also be appreciated by those of skill in the art, the structural repeat unit p together with the amino acid-derived fragment to which it is attached, includes groups Q, and corresponds to the hydrophobic block of the block co-polymer.

Each Q group includes a divalent radical of an amino acid side chain group. In some embodiments, Q includes a side chain from one of the naturally occurring proteinogenic amino acids (other than glycine) or a homolog or derivative thereof. Such amino acid side chain groups include, but are not limited to, glutamic acid (i.e., —CH$_2$CH$_2$CO$_2$H), aspartic acid (i.e., —CH$_2$CO$_2$H), tyrosine (i.e., —CH$_2$(1,4-C$_6$H$_4$)OH), serine (i.e., —CH$_2$OH), threonine (i.e., —CH(CH$_3$)OH), lysine (i.e., —CH$_2$CH$_2$CH$_2$CH$_2$NH$_2$), ornithine (i.e., —CH$_2$CH$_2$CH$_2$NH$_2$), histidine (i.e., —CH$_2$(4-imidazolyl), arginine (i.e., —CH$_2$CH$_2$CH$_2$NHC(=NH)NH$_2$), hydroxyarginine, (i.e., —CH$_2$CH$_2$CH$_2$NHC(=NH)NHOH), or N-(3-hydroxypropyl)aspartamide (i.e., —CH$_2$C(O)NHCH$_2$CH$_2$CH$_2$OH). The two attachment points of the Q group may vary. For example, in the block co-polymer where Q is a mono- or divalent radical of a glutamic acid side chain, the block co-polymer will include a poly(glutamic acid) block and the Q may be groups such as —CH$_2$CH$_2$CO$_2$—, —CH$_2$CH(CO$_2$H)—, and the like. In some embodiments. Q is a mono- or divalent radical of a glutamic acid side chain or an aspartic side chain.

The hydrophobic block of the block co-polymer may be viewed as an amino acid homopolymer block. As a homopolymer, the identity of the Q groups in a particular block co-polymer do not vary at each occurrence. Stated another way, in a block co-polymer of the present technology, Q groups are based on a single amino acid side chain, e.g., that of glutamic acid. Further, in some embodiments, the Q group may be a divalent radical of a derivative of an amino acid side chain in which a single —CH$_2$— group or heteroatom group is deleted (a fragment), added (homolog), or replaced with another heteroatom group containing, e.g., O or N. However, each individual group Q need not have the same attachment points nor be the same derivative of an amino acid side-chain. By way of non-limiting example, where the amino acid homopolymer block is a poly(glutamic acid) block, a portion of the side chains can be unmodified (i.e., having the formula —CH$_2$CH$_2$CO$_2$H), a portion of the side chains are fragments, (e.g., having the formula —CH$_2$CO$_2$— or —CH$_2$CH$_2$C(O)—), a portion are homologs (e.g., having the formula —CH$_2$CH$_2$CH$_2$C(O)O—), and another portion of the side chains have X and/or Z groups attached (e.g., having the formula —CH$_2$CH$_2$C(O)O—). Finally, each Q group need not have the same X and Z groups attached (or null).

In the block copolymer of Formula I, X is a divalent radical linking group Z to group Q, or alternatively, X is taken with Z to be null. When X is taken together with Z to be null, it is meant that the group Q is an unmodified amino acid side chain (i.e., monovalent radical of an amino acid side chain). When X is a divalent linking group, at each occurrence X may be, for example, a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, —N(R')C(O)N(R')alkylene-, —N(R')alkyleneN(R')—, —N(R')alkyleneC(O)N(R')—, —N(R')alkyleneN(R')C(=NR')N(R')—, —N(R')alkyleneN(R')C(=NR')N(R')O—, 3-oxylpyrrolidine-1,3-diyl, —C(O)alkyleneN(R')—, —C(O)alkyleneC(O)N(R')—, —C(O)alkyleneN(R')C(=NR')N(R')—, or —C(O)alkyleneN(R')C(=NR')N(R')O—, wherein R' is independently and at each occurrence H or alkyl. In some embodiments, the alkylene groups are unsubstituted linear alkylene groups such as methylene, ethylene, propylene, butylene, or pentylene. Where X is a bond, Q is attached directly to Z.

In addition to being taken together with X to be null, Z may also independently and at each occurrence be H, alkyl, or a group of Formula II

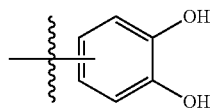

and at least one occurrence of Z is the group of Formula II. Thus, the block co-polymers of the present technology include at least one dihydroxyphenyl moiety. Similarly, $Z^1$ can be H, alkyl, or a group of Formula II; $Z^1$ however may not be null. The percentage of Z groups which are the group of Formula II can vary, depending on the adhesive properties desired. For example, the percentage of Z groups which are the group of Formula II may be about 10%, about 20%, about 30%, about 40%, about 50%, about 60% about 70%, about 80%, about 90%, about 100%, or a range between and including any two of these values. In some embodiments, about 10% to about 100% of the Z groups are the group of Formula II. In a certain embodiment, about 100% of the Z groups are the group of Formula II. Generally, compounds having a higher percentage of Z groups that are the group of Formula II will provide higher amounts of adhesion to surfaces than those with a lower percentage of such groups.

In one embodiment, the groups X and Z are together a dihydroxyphenethylamine group, such as dopamine, L-DOPA, norepinephrine, or epinephrine. For example, the side chains of a poly(glutamic acid) block may be modified to an amide containing groups such as —CH$_2$CH$_2$C(O)N(H)CH$_2$CH$_2$(dihydroxyphenyl).

In some embodiments of the block co-polymer of Formula I, -Q-X—Z is one or more of —CH$_2$CO$_2$H, —CH$_2$CO$_2$CH$_2$(dihydroxyphenyl), —CH$_2$CO$_2$CH$_2$CH$_2$(dihydroxyphenyl), —CH$_2$C(O)NHCH$_2$(dihydroxyphenyl), —CH$_2$C(O)NHCH$_2$CH$_2$(dihydroxyphenyl), —CH$_2$CH$_2$CO$_2$H, —CH$_2$CH$_2$CO$_2$CH$_2$(dihydroxyphenyl), —CH$_2$CH$_2$CO$_2$CH$_2$CH$_2$(dihydroxyphenyl), —CH$_2$CH$_2$C(O)NHCH$_2$(dihydroxyphenyl), —CH$_2$CH$_2$C(O)NHCH$_2$CH$_2$(dihydroxyphenyl), —CH$_2$(1,4-C$_6$H$_4$)OH, —CH$_2$(1,4-C$_6$H$_4$)OCH$_2$(dihydroxyphenyl), —CH$_2$(1,4-C$_6$H$_4$)OCH$_2$CH$_2$(dihydroxyphenyl), —CH$_2$(1,4-C$_6$H$_4$)OC(O)(dihydroxyphenyl), —CH$_2$(1,4-C$_6$H$_4$)OC(O)CH$_2$(dihydroxyphenyl), —CH$_2$(1,4-C$_6$H$_4$)OC(O)CH$_2$CH$_2$(dihydroxyphenyl), —CH$_2$OH, —CH$_2$OCH$_2$(dihydroxyphenyl), —CH$_2$OCH$_2$CH$_2$(dihydroxyphenyl), —CH$_2$OC(O)(dihydroxyphenyl), —CH$_2$OC(O)CH$_2$(dihydroxyphenyl), —CH$_2$OC(O)CH$_2$CH$_2$(dihydroxyphenyl), —CH(CH$_3$)OH, —CH(CH$_3$)OCH$_2$(dihydroxyphenyl), —CH(CH$_3$)OCH$_2$CH$_2$(dihydroxyphenyl), —CH(CH$_3$)OC(O)(dihydroxyphenyl), —CH(CH$_3$)OC(O)CH$_2$(dihydroxyphenyl), —CH(CH$_3$)OC(O)CH$_2$CH$_2$(dihydroxyphenyl), —CH$_2$CH$_2$CH$_2$CH$_2$NH$_2$, —CH$_2$CH$_2$CH$_2$CH$_2$NHCH$_2$(dihydroxyphenyl), —CH$_2$CH$_2$CH$_2$CH$_2$NHCH$_2$CH$_2$(dihydroxyphenyl), —CH$_2$CH$_2$CH$_2$CH$_2$NHC(O)(dihydroxyphenyl), —CH$_2$CH$_2$CH$_2$CH$_2$NHC(O)CH$_2$(dihydroxyphenyl), —CH$_2$CH$_2$CH$_2$CH$_2$NHC(O)CH$_2$CH$_2$(dihydroxyphenyl), —CH$_2$CH$_2$CH$_2$NH$_2$, —CH$_2$CH$_2$CH$_2$NHCH$_2$(dihydroxyphenyl), —CH$_2$CH$_2$CH$_2$NHCH$_2$CH$_2$(dihydroxyphenyl), —CH$_2$CH$_2$CH$_2$NHC(O)(dihydroxyphenyl), —CH$_2$CH$_2$CH$_2$NHC(O)CH$_2$(dihydroxyphenyl), —CH$_2$CH$_2$CH$_2$NHC(O)CH$_2$CH$_2$(dihydroxyphenyl), —CH$_2$CH$_2$CH$_2$NHC(=NH)NH$_2$, —CH$_2$CH$_2$CH$_2$NHC(=NH)NHCH$_2$(dihydroxyphenyl), —CH$_2$CH$_2$CH$_2$NHC(=NH)NHCH$_2$CH$_2$(dihydroxyphenyl), —CH$_2$CH$_2$CH$_2$NHC(=NH)NHC(O)(dihydroxyphenyl), —CH$_2$CH$_2$CH$_2$NHC(=NH)NHC(O)CH$_2$(dihydroxyphenyl), —CH$_2$CH$_2$CH$_2$NHC(=NH)NHC(O)CH$_2$CH$_2$(dihydroxyphenyl), —CH$_2$CH$_2$CH$_2$NHC(=NH)NHOH, —CH$_2$CH$_2$CH$_2$NHC(=NH)NHOCH$_2$(dihydroxyphenyl), —CH$_2$CH$_2$CH$_2$NHC(=NH)NHOCH$_2$CH$_2$(dihydroxyphenyl), —CH$_2$CH$_2$CH$_2$NHC(=NH)NHOC(O)(dihydroxyphenyl), —CH$_2$CH$_2$CH$_2$NHC(=NH)NHOC(O)CH$_2$(dihydroxyphenyl), —CH$_2$CH$_2$CH$_2$NHC(=NH)NHOC(O)CH$_2$CH$_2$(dihydroxyphenyl),

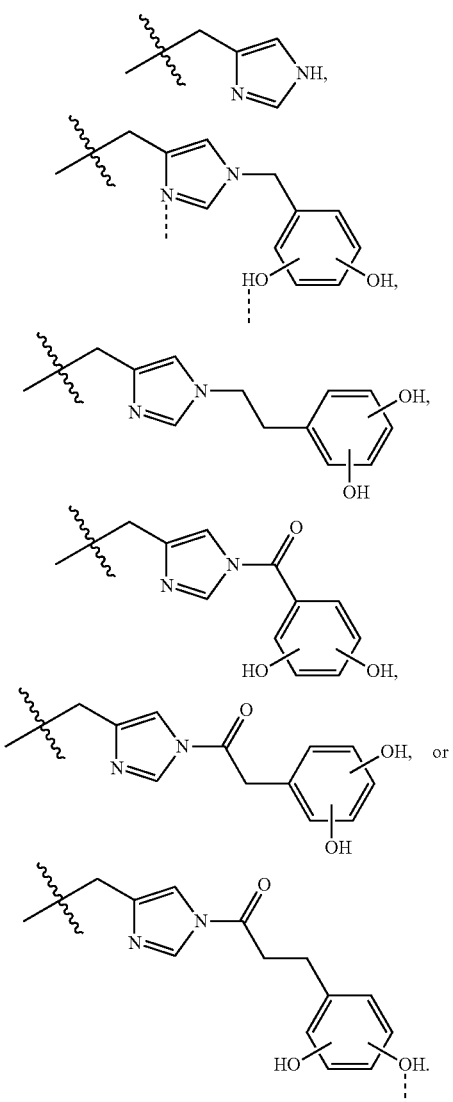

The groups X and Z may together be —N(H)alkyl or —Oalkyl. For example, the side chains of a poly(glutamic acid) block may be amide or ester containing groups such as —CH$_2$CH$_2$C(O)N(H)alkyl or —CH$_2$CH$_2$CO$_2$alkyl. Such groups, may serve to promote micelle formation of the block co-polymer, particularly when longer alkyl chains are used (e.g., C5-C20 alkyl chains).

The groups X and Z may together be amino acid side chain or a portion thereof or a substituted amino acid side chain, such as for example, the amino acid side chain present in lysine, asparagine, hydroxyprolines, glutamine, arginine, or hydroxyarginine. For example, a side chain of a poly (glutamic acid) block may be a group such as —CH$_2$CH$_2$C(O)NHCH$_2$CH$_2$C(O)NH$_2$. Such a group may be considered to be a portion of an asparagine side chain (i.e., decarboxylated asparagine, H$_2$NCH$_2$CH$_2$C(O)NH$_2$) attached to the glutamic acid side chain (—CH$_2$CH$_2$CO$_2$H) of the poly (glutamic acid) block, via an amide bond.

In Formula I, L is a group which links the hydrophilic polymer block to hydrophobic amino acid homopolymer block. The linker may be a bond or any other functional linker group that attaches to both the hydrophilic polymer block and the amino acid homopolymer block. For example, and without limitation, the linker L may be a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, or —N(R')C(O)N(R')alkylene-. In such groups, R' is independently and at each occurrence H or alkyl. Any of the above linkers may include one or more additional functional groups (e.g., esters, amides, oxos, amines, etc.) or heteroatoms (e.g., one or more of N, O, or S), pendent to, or integral to the linker chain. In some embodiments, the alkylene groups are unsubstituted linear alkylene groups such as methylene, ethylene, propylene, butylene, or pentylene. Where L is a bond, an end group of the hydrophilic polymer block may covalently bond directly to an end group of the amino acid homopolymer block.

The repeat units of the block co-polymer of Formula I are repeated m and p times as indicated. Typically, m and p are selected such that neither the hydrophilic block nor the hydrophobic segments dominates to the detriment of the other for which the copolymer is designed. For example, m may be 0, 1, about 5, about 10, about 20, about 50 about 100, about 200, about 300, about 400, about 500, about 600, about 700, about 800, about 900, about 1000, about 1500, about 2000, or a range between and including any two of these values. Independently of m, p may be 1, about 5, about 10, about 20, about 50 about 100, about 200, about 300, about 400, about 500, about 600, about 700, about 800, about 900, about 1000, about 1500, about 2000, about 2500, about 3000, about 3500, about 4000, about 4500, about 5000, about 6000, about 7000, or a range between and including any two of these values. In one embodiment, m is 0 or 1 to about 1000 and p is 1 to about 5000. In another embodiment, m is 0 or 1 to 500 and p is 1 to 1000.

The linking group, L, may be formed upon reaction of an appropriately functionalized hydrophilic polymer with an appropriately functionalized amino acid homopolymer. In one embodiment, L is an —OCH$_2$CH$_2$— group, arising from a reductive amination reaction of an aldehyde terminated poly(ethylene glycol) methyl ether with the N-terminus of an amino acid homopolymer such as polyglutamic acid.

The compounds of Formula I may be prepared by adapting procedures commonly known in the art. For example, commercially available poly(ethylene glycols) with various molecular weights and reactive end groups may be coupled to commercially available amino acid homopolymers, such as poly(glutamic acid), poly(aspartic acid) and the like. In some embodiments, an aldehyde-terminated poly(ethylene glycol) is contacted with poly(glutamic acid), such that the aldehyde group reacts with the N-terminus of poly(glutamic acid). The intermediate imine-linked block co-polymer is reduced with a hydride reagent (e.g., a borohydride reagent such as sodium cyanoborohydride, sodium borohydride, or sodium triacetoxyborohydride; a borane reagent such as pyridine-borane or picoline-borane; a silane reagent such as phenylsilane). Alternatively, the imine-linked block copolymer may also be reduced under catalytic conditions employing hydrogen in conjunction with any number of metal catalysts commonly known in the art (e.g., Pd/C, Rh/C, Ra/Ni, etc.)

The poly(amino acid) block of the block co-polymer includes a plurality of amino acid side chains which may be further modified employing techniques and reagents commonly known in the art. For example, if the poly(amino acid) block is poly(glutamic acid), all or a portion of the carboxylic acid groups present in the side chains may be reacted with reagents which include a dihydroxyphenyl moiety. A wide variety of such reagents may be used, including for example, an alcohol or amine group tethered to a dihydroxyphenyl moiety. Thus, esterification or amidation reactions with such reagents provide a block co-polymer in which dihydroxyphenyl groups are the tethered to the carboxylic acid groups of the glutamic acid side chains. As a brief example, any of the following alcohols and/or amines may be reacted with a carboxylic acid group of a glutamic acid side chain in poly (glutamic acid): trihydroxybenzene, HOCH$_2$(dihydroxyphenyl), HOCH$_2$CH$_2$(dihydroxyphenyl), HOCH$_2$C(O)(dihydroxyphenyl), HOCH$_2$CH$_2$O(dihydroxyphenyl), HOCH$_2$CH$_2$C(O)NH(dihydroxyphenyl), HOCH$_2$CH$_2$C(O)N(H)CH$_2$CH$_2$(dihydroxyphenyl), H$_2$NCH$_2$(dihydroxyphenyl), H$_2$NCH$_2$CH$_2$(dihydroxyphenyl), H$_2$NCH$_2$C(O)(dihydroxyphenyl), H$_2$NCH$_2$CH$_2$O(dihydroxyphenyl), H$_2$NCH$_2$CH$_2$C(O)NH(dihydroxyphenyl), H$_2$NCH$_2$CH$_2$C(O)N(H)CH$_2$(dihydroxyphenyl), etc. As will be appreciated by those of skill in the art, the hydroxyl groups of the dihydroxyphenyl moiety may optionally be protected using a suitable protection reagent (e.g., silyl halides and pseudohalides, such as trimethylsilyl chloride and tert-butyldimethylsilyl triflate) prior to reaction with the carboxylic acid groups, and subsequently deprotected using established methods.

As introduced above, the carboxylic acid groups may also be modified with amines (e.g., C-5 to C-20 alkylamines such as hexylamine, heptylamine, octylamine, decylamine, hexadecylamine, and the like) and alcohols (e.g., alkanols such as octanol, decanol, tridecanol, and the like) which do not include dihydroxyphenyl groups. Such amines and alcohols will impart additional hydrophobicity to the amino acid homopolymer block, aiding in micelle formation.

The carboxylic acid groups of the glutamic acid side chains of the poly(glutamic acid) block may be modified with functionalized amines and alcohols, as well. For example, the such carboxylic acid groups of the glutamic acid side chains may be modified with amines and alcohols which themselves include a portion of an amino acid side chain. For example, carboxylic acid side chain groups of a poly(glutamic acid) block may be modified with amines such as H$_2$NCH$_2$CH$_2$CH$_2$CH$_2$NH$_2$ (decarboxylated lysine), H$_2$NCH$_2$CH$_2$C(O)NH$_2$ (decarboxylated asparagine), H$_2$NCH$_2$CH$_2$CH$_2$C(O)NH$_2$ (decarboxylated glutamine), H$_2$NCH$_2$CH$_2$CH$_2$CH$_2$NHC(=NH)NH$_2$ (decarboxylated arginine), H$_2$NCH$_2$CH$_2$CH$_2$CH$_2$NHC(=NH)NHOH (decarboxylated hydroxyarginine), 3-hydroxyproline, or alcohols such as HOCH$_2$CH$_2$CH$_2$CH$_2$NH$_2$ (analog of decarboxylated lysine), HOCH$_2$C(O)NH$_2$ (analog of decarboxylated asparagine), HOCH$_2$CH$_2$C(O)NH$_2$ (analog of decarboxylated glutamine), HOCH$_2$CH$_2$CH$_2$CH$_2$NHC(=NH)NH$_2$ (analog of decarboxylated arginine), or HOCH$_2$CH$_2$CH$_2$CH$_2$NHC(=NH)NHOH (analog of decarboxylated hydroxyarginine).

While the above examples have are generally directed to the modification of the carboxylic acid groups of carboxylic acid-containing amino acid side chains such as those found in poly(glutamic acid) and poly(aspartic acid), one of ordinary skill in the art will readily recognize poly(amino acid)s with functionality other than carboxylic acid groups in the side chain can also be used. For example, side chains with amino groups (e.g., polylysine or polyornithine) or alcohol groups (e.g., polyserine, polythreonine, polyhydroxyarginine, etc.) may can be alkylated, or acylated using minor modifications to the reagents and processes described for the modification of carboxylic acid groups.

The highly flexible synthetic procedures described herein allow for the preparation of a variety of block co-polymers with tailored properties. For example, the block copolymers may be designed to form micelles rather than hydrogels and vice versa. As indicated above, micellar structures may be used to prevent oxidation during storage of the block co-polymers (or adhesives prepared therefrom). The following structural features of the block co-polymers are readily varied: the identity of the amino acid in the amino acid homopolymer block; the molecular weights of the hydrophilic polymer block or the hydrophobic amino acid homopolymer block; and the proportion and type of functionalization of the amino acid side chains in the homopolymer block. With regard to amino acid side chain functionalization, such groups may be modified to include varying levels of: dihydroxyphenyl moieties, amino acid side chain mimetics, and alkyl substitutents.

In accordance with another aspect, the present technology provides a block co-polymer including: a first block of poly(ethylene glycol) having a number average molecular weight of about 1,000 to about 10.000; and a second block of a poly(amino acid) homopolymer having a number average molecular weight of about 500 to about 100,000, wherein the poly(amino acid) homopolymer comprises dihydroxyphenyl groups linked to one or more of the amino acid side chain groups. In some embodiments, the amino acid side chain groups are selected from imidazoles, amines, hydroxyls, and carboxylates, guanidines, and hydroxyguanidines. Non-limiting examples of amino acids which include such groups are glutamic acid, aspartic acid, tyrosine, serine, threonine, lysine, ornithine, histidine, arginine, hydroxyarginine, N-(3-hydroxypropyl)aspartamide, and substituted derivatives thereof.

Any of the block co-polymers described herein may themselves be adhesives, or may used to prepare adhesives. For example, the block co-polymers may be dispersed in a solvent and applied to a substrate to be adhered. The solvent may be any biocompatible solvent or solvent system. In some embodiments, the solvent is water, ethanol, aqueous ethanol, or an aqueous buffer solution such as, but not limited to, phosphate buffer solution (PBS). The substrate may be a wetted or moist substrate, such as wetted or moistened with water or other aqueous liquid. The adhesives may be applied to any substrate including, but not limited to metal, paper, glass, wood, plastic, and tissues. Examples of tissues include, but are not limited to bone (and tooth), skin, and organ tissues. In some embodiments, the adhesives of the present technology also include a peroxide, such as hydrogen peroxide or benzoyl peroxide. Such a peroxide may be added at the time of application of the adhesive. Without wishing to be bound by any particular theory, it is believed that peroxide may aid in cross-linking or curing of the adhesive by oxidation of the dihydroxyphenyl groups in the block co-polymer to ortho-quinone groups. In some embodiments, the adhesives of the present technology are dispersed in an aqueous buffer solution and include peroxide such as, but not limited to, hydrogen peroxide or benzoyl peroxide.

In some embodiments, the bioadhesive polymers of the present technology may be used to form micelles. Thus, certain compounds of Formula I, e.g., may exhibit a shell of PEG blocks on their outer surface, when exposed to an aqueous medium and a predominantly hydrophobic core. Thus, a suitably buffered aqueous solution containing a bioadhesive polymer is stirred or sonicated to promote formation of the micelles. The final polymer concentration is above its critical micelle concentration. Organic solvent and other small molecule impurities are removed by dialysis against distilled or buffered water with a membrane having particle size cutoff below the micelle diameter.

The micelles may include other additives such as, but not limited to buffering agents, salts, surfactants, viscosity modifiers, stabilizers (against degradation due to freezing or contamination, for example), anti-freeze agents, diluents, encoding agents, and the like. Among such additives may be mentioned glycerin, dimethylsulfoxide, ethylene glycol, various gelatins both natural and synthetic, and polyols such as sorbitol. The aqueous vehicle may be buffered at a desired pH. For example, the pH may be at, or about 7. The aqueous vehicle may include sodium chloride at physiological saline concentration (e.g. 0.9 w/v % saline).

In accordance with another aspect, the present technology provides a method of adhering together at least two substrates, the method including: applying an adhesive of Formula I to at least one substrate; and adhering together the substrates, wherein the adhesive includes the block copolymer of Formula I. In some embodiments, the adhesive is contained in micelles and optionally containing an imaging agent. In some embodiments, the imaging agent is selected from a fluorescent dye, a radiographic, and an ultrasonic or MRI contrast agent.

The present technology, thus generally described, will be understood more readily by reference to the following Examples, which is provided by way of illustration and is not intended to be limiting of the present technology.

EXAMPLES

Example 1

Preparation of mPEG-PGA Copolymers Via Reductive Amination

Starting materials. Monomethoxypoly(ethylene glycol) ("mPEG") of average $M_n$ ~2,000 (mPEG 2000) or ~5,000 (mPEG 5000), and the sodium salt of poly(L-glutamic acid) ("PGA") of molecular weight ranges of 750-5,000, 2,000-15,000, 15,000-50,000, and 50,000-100,000 are obtained from Sigma-Aldrich (St Louis, Mo.). mPEGs and PGAs of other molecular weights are commercially available elsewhere (e.g., Creative PEGWorks, Winston-Salem, N.C.). Oxidation of mPEGs to the corresponding mPEG-aldehydes may be accomplished according to published methods, such as those described by Dou, H, et al. *Chem. Biol. Drug Res.* 2007, 69, 132-138. Alternatively, certain mPEG-aldehydes are commercially available (e.g., Creative PEGWorks, Winston-Salem, N.C.).

The conjugation of mPEG-aldehydes to the free amino groups of PGA via reductive amination to form a mPEG-PGA copolymer is achieved through adaptation of methods previously described for the mono-N-terminal PEGylation of granulocyte colony stimulating factor (G-CSF) and insulin by reductive amination. Dou, H., et al. *Chem. Biol. Drug Res.* 2007, 69, 132-138 and Kinstler, O., et al. *Adv. Drug Deliv. Rev.* 2002, 54, 477-485.

A general procedure for the preparation of mPEG-PGA block co-polymers via reductive amination is as follows. A mixture of the sodium salt of PGA (5 mg/mL) in 100 mM sodium acetate, pH 5, and sodium cyanoborohydride (20 mM) is stirred in an ice bath. A five-fold molar excess of mPEG-aldehyde is added and the mixture is stirred overnight. The mixture is adjusted to pH 3 with hydrochloric acid (10 mM). The mPEG-PGA copolymer may be purified by collecting the precipitate and washing with water, by ion exchange chromatography or by dialysis. A general synthesis for a mPEG-PGA copolymer (3) from an mPEG aldehyde (1) and PGA (2) is illustrated in FIG. 1. Residual water may be removed by freeze-drying.

The above procedure may be modified in a number of ways, including the use of mPEG-aldehydes and PGAs of varying molecular weights. Homopolymeric amino acids with carboxylate side chains such as poly(aspartic acid) may be used in place of PGA. Homopolymeric amino acids with amine side chains, such as poly($\epsilon$-CBZ-L-lysine) may be used in place of PGA. Poly($\epsilon$-CBZ-L-lysine), Mn=5,800 is commercially available (Sigma-Aldrich, St. Louis, Mo.). In this regard, after reductive amination with mPEG-aldehyde and purification in an analogous manner to that described above, the CBZ protecting groups may be removed by contacting block co-polymer with trifluoroacetic acid and hydrogen bromide (33% in acetic acid, 4 equivalents per mole of CBZ groups). After addition of excess diethyl ether, the precipitate is washed with additional ether and dried under reduced pressure.

Example 2

Preparation of Bioadhesive Polymers from mPEG-PGA Copolymers

Starting materials. Amines, including dihydroxyphenyl-substituted amines such as 3,4-dihydroxyphenethylamine (dopamine) and 3,4-dihydroxybenzylamine, are commercially available from Sigma-Aldrich.

Acylation of amines with the free carboxyl groups of the mPEG-PGA conjugate from Example 1 is accomplished by adapting standard peptide coupling methods previously described for the N-acylation of small molecule therapeutics with PGA. See, for example, Kumar, A. M. et al. U.S. Pat. No. 7,399,860.

A general procedure for the preparation of bioadhesive polymers from mPEG-PGA copolymer and a dihydroxyphenyl-substituted amine (dopamine) is as follows. A mixture of the mPEG-PGA copolymer (Example 1), amine (1 mole equivalent per mole of free carboxyl group to be acylated), dimethylaminopyridine (3 mole equivalents per mole of amine), diisopropylcarbodiimide (1.3 mole equivalents per mole of dihydroxyphenyl-substituted amine), and dimethylformamide is stirred overnight. After addition of aqueous sodium chloride solution (10%), the bioadhesive polymer is purified by washing with water or by chromatographic methods. The acylation of dopamine with the mPEG-copolymer (3) to provide bioadhesive polymer (4) is illustrated in FIG. 1.

The diblock bioadhesive polymer (4), which includes a hydrophilic PEG block and hydrophobic dihydroxyphenyl-modified PGA block, readily forms micelles. The micelles exhibit a shell of PEG blocks on their outer surface exposed to aqueous medium (e.g., water), and a predominantly hydrophobic core that contributes to the protection of dihydroxyphenyl moieties (e.g., from oxidation by air) prior to use in adhesive applications.

The above procedure is applicable to a wide variety of amines and alcohols other than dopamine (which may or may not include dihydroxyphenyl moieties). Further, the stoichiometry of the above procedure may be tailored as to leave unreacted carboxylate groups. All or a portion of the unreacted carboxylate groups may be then be reacted with different amines and/or alcohols. The amines and/or or alcohols may be structurally simple, for example alkylamines (e.g., octylamine) and/or alkanols (e.g., decylamine). Alternatively, the amines and/or alcohols maybe structurally complex, such as amines and/or alcohols which mimic the side chains present in amino acids, such as asparagine, hydroxyprolines, glutamine, arginine, and hydroxyarginine.

Example 3

Preparation of Micelles and Hydrogels

As an amphiphilic block co-polymer having a hydrophilic block and a hydrophobic block, bioadhesive polymer 4 forms micelles. These micelles exhibit a shell of PEG blocks on their outer surface exposed to the aqueous medium and a predominantly hydrophobic core. Treatment of a mixture of bioadhesive polymer 4, at a concentration above its critical micelle concentration, and phosphate buffered saline (PBS; pH 7.4), with or without addition of a fluorescent dye or a radiographic, ultrasonic or MRI contrast agent to aid in tracking micelle localization in vivo, with ultrasonic irradiation results in micelle formation.

Alternatively, if the catechol-containing block of bioadhesive polymer 4 is highly hydrophilic then a hydrogel forms upon evaporation of water from an aqueous solution of 4.

Example 4

Application of Bioadhesive Micelles and Hydrogels

Micelles or hydrogels of bioadhesive polymer 4 (optionally with an imaging agent as in Example 3) are applied to one or both surfaces of the tissues and/or materials to be joined. Curing can be accelerated by simultaneous application of an aqueous solution of hydrogen peroxide to the surfaces to be joined.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A block co-polymer of Formula I $$\text{I}$$

wherein,

R is H or alkyl;

Y is —O—, —N(H)—, or —NC(O)alkylene-;

L is a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, or —N(R')C(O)N(R')alkylene-;

Q is a mono- or divalent radical of an amino acid side chain selected from a glutamic acid side chain, an aspartic acid side chain, a tyrosine side chain, a serine side chain, a threonine side chain, a lysine side chain, an ornithine side chain, a histidine side chain, an arginine side chain, a hydroxyarginine side chain, or an N-(3-hydroxypropyl)aspartamide side chain;

X is independently and at each occurrence a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, —N(R')C(O)N(R')alkylene-, —N(R')alkyleneN(R')—, —N(R')alkyleneC(O)N(R')—, —N(R')alkyleneN(R')C(=NR')N(R')—, —N(R')alkyleneN(R')C(=NR')N(R')O—, 3-oxylpyrrolidine-1,3-diyl, —C(O)alkyleneN(R')—, —C(O)alkyleneC(O)N(R')—, —C(O)alkyleneN(R')C(=NR')N(R')—, —C(O)alkyleneN(R')C(=NR')N(R')O—, or when taken together with Z is null;

Z is independently and at each occurrence selected from the group consisting of H, alkyl, and a group of Formula II $$\text{II}$$

or when taken together with X is null, wherein at least one occurrence of Z is the group of Formula II;

$Z^1$ is selected from the group consisting of H, alkyl, and a group of Formula II as defined above;

R' is independently and at each occurrence H or alkyl;

m is an integer from 0 to about 2000; and p is an integer from 1 to about 7000.

2. The block co-polymer of claim 1, wherein Y is —O—.

3. The block co-polymer of claim 1, wherein L is —O—CH$_2$CH$_2$— or —N(R')CH$_2$CH$_2$—.

4. The block co-polymer of claim 1, wherein R is H, methyl, or ethyl.

5. The block co-polymer of claim 1, wherein m is 1 to about 1000.

6. The block co-polymer of claim 1, wherein p is 1 to about 5000.

7. The block co-polymer of claim 1, wherein Q is a mono- or divalent radical of a glutamic acid side chain or an aspartic acid side chain.

8. The block co-polymer of claim 1, wherein —X—Z is null.

9. The block co-polymer of claim 1, wherein —X—Z is —N(H)alkyl or —Oalkyl.

10. The block co-polymer of claim 1, wherein —X—Z is a dihydroxyphenethylamine group.

11. The block co-polymer of claim 10, wherein the dihydroxyphenethylamine group is dihydroxyphenethylamine, L-DOPA, norepinephrine, or epinephrine.

12. The block co-polymer of claim 1, wherein -Q-X—Z is one or more of —CH$_2$CO$_2$H, —CH$_2$CO$_2$CH$_2$(dihydroxyphenyl), —CH$_2$CO$_2$CH$_2$CH$_2$(dihydroxyphenyl), —CH$_2$C(O)

NHCH₂(dihydroxyphenyl), —CH₂C(O)NHCH₂CH₂(dihydroxyphenyl), —CH₂CH₂CO₂H, —CH₂CH₂CO₂CH₂(dihydroxyphenyl), —CH₂CH₂CO₂CH₂CH₂(dihydroxyphenyl), —CH₂CH₂C(O)NHCH₂(dihydroxyphenyl), —CH₂CH₂C(O)NHCH₂CH₂(dihydroxyphenyl), —CH₂(1,4-C₆H₄)OH, —CH₂(1,4-C₆H₄)OCH₂(dihydroxyphenyl), —CH₂(1,4-C₆H₄)OCH₂CH₂(dihydroxyphenyl), —CH₂(1,4-C₆H₄)OC(O)(dihydroxyphenyl), —CH₂(1,4-C₆H₄)OC(O)CH₂(dihydroxyphenyl), —CH₂(1,4-C₆H₄)OC(O)CH₂CH₂(dihydroxyphenyl), —CH₂OH, —CH₂OCH₂(dihydroxyphenyl), —CH₂OCH₂CH₂(dihydroxyphenyl), —CH₂OC(O)(dihydroxyphenyl), —CH₂OC(O)CH₂(dihydroxyphenyl), —CH₂OC(O)CH₂CH₂(dihydroxyphenyl), —CH(CH₃)OH, —CH(CH₃)OCH₂(dihydroxyphenyl), —CH(CH₃)OCH₂CH₂(dihydroxyphenyl), —CH(CH₃)OC(O)(dihydroxyphenyl), —CH(CH₃)OC(O)CH₂(dihydroxyphenyl), —CH(CH₃)OC(O)CH₂CH₂(dihydroxyphenyl), —CH₂CH₂CH₂CH₂NH₂, —CH₂CH₂CH₂CH₂NHCH₂(dihydroxyphenyl), —CH₂CH₂CH₂CH₂NHCH₂CH₂(dihydroxyphenyl), —CH₂CH₂CH₂CH₂NHC(O)(dihydroxyphenyl), —CH₂CH₂CH₂CH₂NHC(O)CH₂(dihydroxyphenyl), —CH₂CH₂CH₂NHC(O)CH₂CH₂(dihydroxyphenyl), —CH₂CH₂CH₂NH₂, —CH₂CH₂CH₂NHCH₂(dihydroxyphenyl), —CH₂CH₂CH₂NHCH₂CH₂(dihydroxyphenyl), —CH₂CH₂CH₂NHC(O)(dihydroxyphenyl), —CH₂CH₂CH₂NHC(O)CH₂(dihydroxyphenyl), —CH₂CH₂CH₂NHC(O)CH₂CH₂(dihydroxyphenyl), —CH₂CH₂CH₂NHC(=NH)NH₂, —CH₂CH₂CH₂NHC(=NH)NHCH₂(dihydroxyphenyl), —CH₂CH₂CH₂NHC(=NH)NHCH₂CH₂(dihydroxyphenyl), —CH₂CH₂CH₂NHC(=NH)NHC(O)(dihydroxyphenyl), —CH₂CH₂CH₂NHC(=NH)NHC(O)CH₂(dihydroxyphenyl), —CH₂CH₂CH₂NHC(=NH)NHC(O)CH₂CH₂(dihydroxyphenyl), —CH₂CH₂CH₂NHC(=NH)NHOH, —CH₂CH₂CH₂NHC(=NH)NHOCH₂(dihydroxyphenyl), —CH₂CH₂CH₂NHC(=NH)NHOCH₂CH₂(dihydroxyphenyl), —CH₂CH₂CH₂NHC(=NH)NHOC(O)(dihydroxyphenyl), —CH₂CH₂CH₂NHC(=NH)NHOC(O)CH₂(dihydroxyphenyl), —CH₂CH₂CH₂CH₂NHC(=NH)NHOC(O)CH₂CH₂(dihydroxyphenyl),

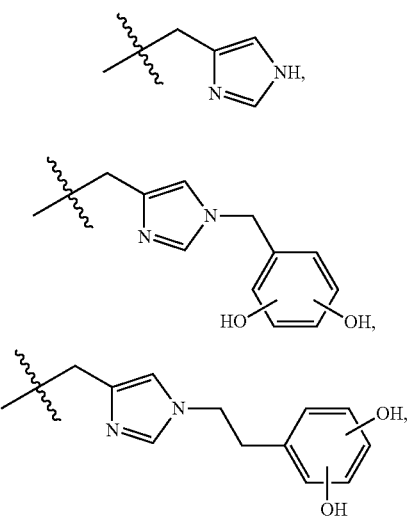

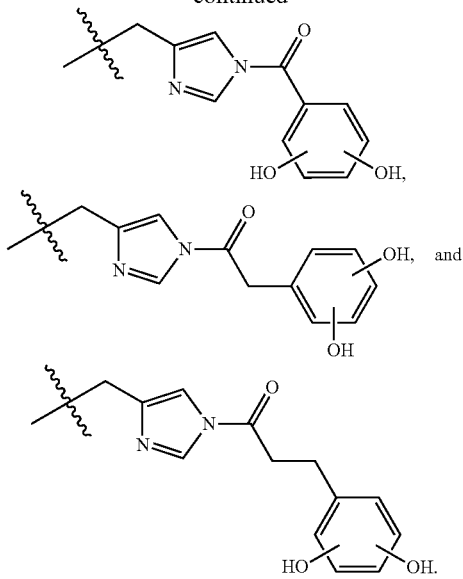

13. The block co-polymer of claim 1, wherein about 10% to about 100% of the Z groups are the group of Formula II.

14. A block co-polymer comprising:
a first block of poly(ethylene glycol) having a number average molecular weight of about 1,000 to about 10,000; and
a second block of a poly(amino acid) homopolymer having a number average molecular weight of about 500 to about 100,000,
wherein the poly(amino acid) homopolymer comprises dihydroxyphenyl groups linked to one or more of the amino acid side chain groups;
wherein the amino acid side chain groups are selected from the group consisting of imidazoles, amines, hydroxyls, carboxylates, guanidines, and hydroxyguanidines.

15. An adhesive comprising a block co-polymer of Formula I

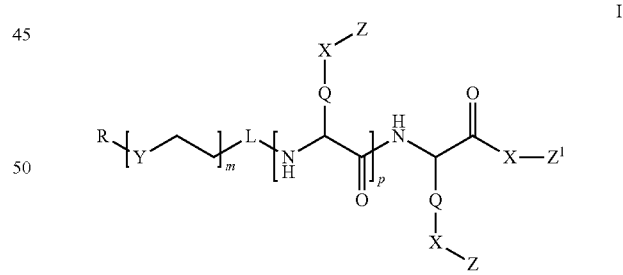

wherein,
R is H or alkyl;
Y is —O—, —N(H)—, or —NC(O)alkylene-;
L is a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, or —N(R')C(O)N(R')alkylene-;
Q is a mono- or divalent radical of an amino acid side chain selected from a glutamic acid side chain, an aspartic acid side chain, a tyrosine side chain, a serine side chain, a threonine side chain, a lysine side chain, an ornithine side chain, a histidine side chain, an arginine side chain, a hydroxyarginine side chain, or an N-(3-hydroxypropyl)aspartamide side chain;

X is independently and at each occurrence a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, —N(R')C(O)N(R')alkylene-, —N(R')alkyleneN(R')—, —N(R')alkyleneC(O)N(R')—, —N(R')alkyleneN(R')C(=NR')N(R')—, —N(R')alkyleneN(R')C(=NR')N(R')O—, 3-oxylpyrrolidine-1,3-diyl, —C(O)alkyleneN(R')—, —C(O)alkyleneC(O)N(R')—, —C(O)alkyleneN(R')C(=NR')N(R')—, —C(O)alkyleneN(R')C(=NR')N(R')O—, or when taken together with Z is null;

Z is independently and at each occurrence selected from the group consisting of H, alkyl, and a group of Formula II

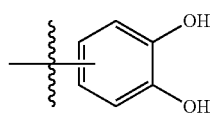

or when taken together with X is null, wherein at least one occurrence of Z is the group of Formula II;

$Z^1$ is selected from the group consisting of H, alkyl, and a group of Formula II as defined above;

R' is independently and at each occurrence H or alkyl;

m is an integer from 0 to about 2000; and p is an integer from 1 to about 7000.

16. The adhesive of claim 15 further comprising a peroxide.

17. The adhesive of claim 16, wherein the peroxide is hydrogen peroxide.

18. A method of adhering together at least two substrates, the method comprising:

applying an adhesive of Formula I to at least one substrate; and adhering together the substrates, wherein the adhesive has the Formula I

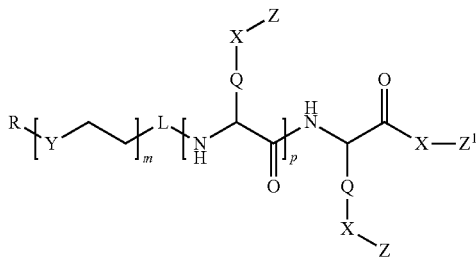

wherein,

R is H or alkyl;

Y is —O—, —N(H)—, or —NC(O)alkylene-;

L is a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, or —N(R')C(O)N(R')alkylene-;

Q is a mono- or divalent radical of an amino acid side chain selected from a glutamic acid side chain, an aspartic acid side chain, a tyrosine side chain, a serine side chain, a threonine side chain, a lysine side chain, an ornithine side chain, a histidine side chain, an arginine side chain, a hydroxyarginine side chain, or an N-(3-hydroxypropyl)aspartamide side chain;

X is independently and at each occurrence a bond, an alkylene, —O—, —Oalkylene-, —N(R')—, —N(R')alkylene-, —C(O)—, —C(O)alkylene-, —C(O)N(R')—, —C(O)N(R')alkylene-, —C(O)O—, —C(O)Oalkylene-, —N(R')C(O)O—, —N(R')C(O)Oalkylene-, —OC(O)N(R')alkylene-, —N(R')C(O)N(R')—, —N(R')C(O)N(R')alkylene-, —N(R')alkyleneN(R')—, —N(R')alkyleneC(O)N(R')—, —N(R')alkyleneN(R')C(=NR')N(R')—, —N(R')alkyleneN(R')C(=NR')N(R')O—, 3-oxylpyrrolidine-1,3-diyl, —C(O)alkyleneN(R')—, —C(O)alkyleneC(O)N(R')—, —C(O)alkyleneN(R')C(=NR')N(R')—, —C(O)alkyleneN(R')C(=NR')N(R')O—, or when taken together with Z is null;

Z is independently and at each occurrence selected from the group consisting of H, alkyl, and a group of Formula II

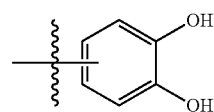

or when taken together with X is null, wherein at least one occurrence of Z is a group of Formula II;

$Z^1$ is selected from the group consisting of H, alkyl, and a group of Formula II as defined above;

R' is independently and at each occurrence H or alkyl; and m is an integer from 0 to about 2000; and p is an integer from 1 to about 7000.

19. The method of claim 18, wherein the substrate is a wetted substrate.

20. The method of claim 18, wherein the substrate is a tissue selected from bone tissue, tooth tissue, skin tissue, or organ tissue.

\* \* \* \* \*

UNITED STATES PATENT AND TRADEMARK OFFICE
CERTIFICATE OF CORRECTION

Page 1 of 2

PATENT NO. : 8,907,045 B2
APPLICATION NO. : 13/823291
DATED : December 9, 2014
INVENTOR(S) : Klein et al.

It is certified that error appears in the above-identified patent and that said Letters Patent is hereby corrected as shown below:

On the Title Page, insert -- 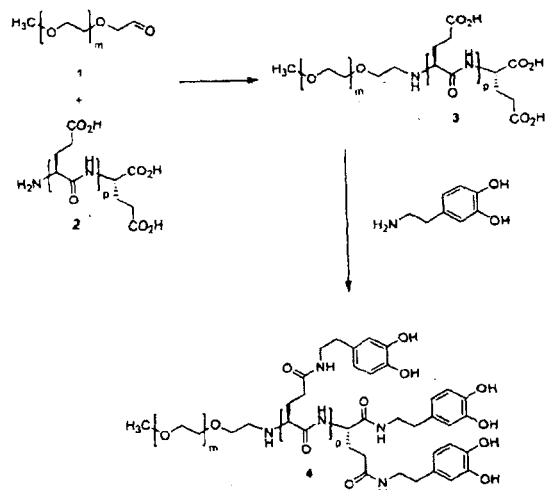 --.

In the Specification

In Column 1, Line 7, delete "stage application" and insert -- stage filing application under 35 U.S.C. §371 --, therefor.

In Column 6, Line 59, delete "DRAWINGS" and insert -- DRAWING --, therefor.

In Column 8, Line 21, delete "Disbustituted" and insert -- Disubstituted --, therefor.

In Column 8, Line 40, delete "Thus." and insert -- Thus, --, therefor.

In Column 8, Line 48, delete "carboxy" and insert -- carboxyl --, therefor.

Signed and Sealed this
First Day of December, 2015

Michelle K. Lee
*Director of the United States Patent and Trademark Office*

CERTIFICATE OF CORRECTION (continued)
U.S. Pat. No. 8,907,045 B2

In Column 10, Line 23, delete "embodiments." and insert -- embodiments, --, therefor.

In Column 12, Line 67, delete "C5-C20" and insert -- $C_5$-$C_{20}$ --, therefor.

In Column 14, Line 40, delete "C-5 to C-20" and insert -- $C_{-5}$ to $C_{-20}$ --, therefor.

In Column 15, Line 10, delete "may can be" and insert -- can be --, therefor.

In Column 15, Line 29, delete "substitutents." and insert -- substituents. --, therefor.

In Column 15, Line 33, delete "10.000;" and insert -- 10,000; --, therefor.

In Column 16, Line 16, delete "to" and insert -- to, --, therefor.